US005185023A

United States Patent [19]

Webb

[11] Patent Number: 5,185,023
[45] Date of Patent: Feb. 9, 1993

[54] PROCESS FOR THE PRODUCTION OF MELLEIN AND 4-HYDROXYMELLEIN

[76] Inventor: Roger S. Webb, Rte. 1, Box 281-38, Micanopy, Fla. 32667

[21] Appl. No.: 698,517

[22] Filed: May 10, 1991

[51] Int. Cl.$^5$ .................... A01N 63/04

[52] U.S. Cl. .................... 504/117; 47/57.5; 47/58; 435/30; 504/292

[58] Field of Search .................... 47/58, 57.5; 435/30; 71/65, 66, 79, 88

[56] References Cited

U.S. PATENT DOCUMENTS

| | | | |
|---|---|---|---|
| 3,849,104 | 11/1974 | Daniel et al. | 71/65 |
| 3,999,973 | 12/1976 | Templeton | 71/79 |
| 4,162,912 | 7/1979 | Charudattan | 71/79 |
| 4,626,271 | 12/1986 | Gleason | 71/66 |
| 4,915,726 | 4/1990 | Bewick et al. | 71/79 |

OTHER PUBLICATIONS

Venkatasubbaiah, P., T. B. Sutton, W. S. Chilton (1991) "Effect of Phytotoxins Produced by *Botryosphaeria obtusa*, the Cause of Black Rot of Apple Fruit and Frog-eye Leaf Spot," Phytopathology 81(3):243-247.

Webb, R. S. (1983) "Seed Capsule Abortion and Twig Dieback of *Eucalyptus camaldulensis* in South Florida Produced by *Botryosphaeria ribis*, Plant Disease" 67(1):108-109.

Moore, J. H., N. D. David, U. L. Diener (1972) "Mellein and 4-Hydroxymellein Production by *Aspergillis ochraceus* Wilhelm," Appl. Microbiology 23(6):1067-1072.

Cole, R. J., J. H. Moore, N. D. Davis, J. W. Kirksey, U. L. Diener (1971) "4-Hydroxymellein: A New Metabolite of *Aspergillus ochraceus*," J. Agr. Food Chem. 19(5):909-911.

Weisskopf, M. (1988) "A Pesticide Peril in A Land of Plenty," The Washington Post National Weekly Edition 5(47):10-11.

Fleming, M. H. (1987) "Agricultural chemicals in ground water: Preventing contamination by removing barriers against low-input farm management," Amer. J. Alternative Agriculture 2(3):124-130.

Ramons, L. J., S. P. Lara, R. T. McMillan, Jr., K. R. Narayanan (1991) "Tip Dieback of Mango (*Mangifera indica*) caused by *Botryosphaeria ribis*," Plant Disease 75(3):315-318.

*Primary Examiner*—Richard L. Raymond
*Assistant Examiner*—B. Bembenick
*Attorney, Agent, or Firm*—Saliwanchik & Saliwanchik

[57] ABSTRACT

The subject invention relates to a novel means of producing mellein and 4-hydroxymellein. The subject invention further concerns a novel means for introducing phytotoxin, disrupting nutrient flow, and inducing selective mortality for population control of a pest plant species.

8 Claims, No Drawings

PROCESS FOR THE PRODUCTION OF MELLEIN AND 4-HYDROXYMELLEIN

BACKGROUND OF THE INVENTION

Beneficial uses of microorganisms are well known in the art and have been documented at great length. Many patents have issued which claim new microbial processes pertaining to the production of antibiotics, enzymes, ethanol, and a multitude of other useful products. Microorganisms are also used to clean up toxic wastes and oil spills, mill pests, recover minerals, and provide nutrients to plants. It has been known for many years that some organisms produce compounds which are toxic to other organisms. The production of the antimicrobial compound penicillin by penicillium mold is one such example.

Microorganisms are particularly attractive candidates for use in making and delivering organic compounds because they can be extremely efficient and safe. The modern tools of genetic engineering have greatly enhanced the ability to exploit the efficiency and relative safety of microbes. Even in the absence of genetic manipulation, however, microbes can perform highly specific tasks which make them indispensable in certain applications. Thus, there is a constant ongoing search in many areas of research for new microbes with specific advantageous properties. The subject invention concerns the discovery of one such microbe.

The tree species *Melaleuca quinquenervia* (Cam.) Blake (Melaleuca) is an exotic pest species which is native to Australia and was introduced into Florida in the early 1900's as an ornamental tree and possibly as a commercial source of wood. Several of Melaleuca's innate characteristics have facilitated its spread throughout South Florida. Melaleuca grows more densely in Florida than in Australia and "crowds out" native plants. Prolific seed production, fire adaptation and release from natural competition, insect feeding and disease further abet its competitive ability. The Melaleuca may become a large tree exceeding 50 feet in height. The tree may have a single trunk or have multiple stems arising from the base of the tree. The bark covering the trunk is white to cream-colored and is very thick and soft, and easily peels in multiple layers from the tree. The tree is easily recognized when flowering, being covered with clusters of white flowers born on the ends of the twigs. Melaleuca flowers throughout the year in Florida, with heavier blooms reported during the wet season with lighter blooms occurring throughout the winter. Individual trees have been reported to bloom as many as five times a year and an individual branch may have three or more blooms each year. Seed capsules which are formed on the flower spike, are from 0.1 to 0.2 inches long and are short and cylindrical. Each capsule, which contains over 200 seeds, may remain attached to the branch for an extended period of time.

A large, mature melaleuca tree has a high reproductive potential as the branches contain millions of seeds stored in the capsules. By flowering three to five times yearly, large numbers of seedlings are produced. These seedlings can, in turn, produce seeds within two to three years, and a mature tree can store over 20 million seeds. Encroachment into ecosystems formerly devoid of Melaleuca is irreversible, permanently replacing natural plant communities and the animals that live in them. Melaleuca was planted from seeds obtained from Australia in the early 1900's at two coastal locations. The present distribution of melaleuca is predominantly centered around the areas of original introduction. Its spread was enhanced through its use as wind breaks and fence rows, and its popularity as a fast growing ornamental. Canals have most likely facilitated the spread of the buoyant seeds in to the interior of conservation areas where relatively undisturbed inland wetlands have been invaded. Sites conducive to Melaleuca development are usually poorly-drained areas which have high water table levels or are flooded periodically each year. These sites comprise much of the ecologically-sensitive wetland areas of South Florida, including the Everglades National Park, the Big Cypress Preserve, and the Loxahatchee National Wildlife Refuge.

Melaleuca is highly resistant to stress, including herbicides and fire. Not only is this species physically resistant to fire, but the seed capsules are stimulated to open by the extreme heat and drying produced by fire. The trees grow rapidly, even when completely submerged in flood waters for periods of six months or longer, and they resume vigorous growth after the water recedes.

Melaleuca has been identified as a potential threat to South Florida's water supply. Future spread of melaleuca throughout the Everglades has the potential to impact regional surface water supplies by replacing open grassy paries with forest.

A task force assigned to study the melaleuca problem has concluded:

"It is the consensus opinion of the [task force] that the uncontrolled expansion of melaleuca constitutes one of the most serious ecological threats to the biological integrity of South Florida's natural systems."

Control of this encroachment is a formidable task, even when chemical herbicides are applied either to individual trees or to groups of trees by aerial spraying. Eradication frequently requires two or three applications of herbicides which increases herbicidal contamination of wetlands. Thus, chemical weed control programs are seriously inadequate for the control of Melaleuca.

Also, the use of chemical pesticides in agriculture is currently a major concern in the U.S. For example, pesticides are being blamed for an epidemic of cancer in children and young adults in the San Joaquin Valley (Weisskopf, M. [1988] The Washington Post Weekly Edition 5(47):10-11, Washington, D.C.). New technologies in detection methods are enabling researchers to find pesticides in the environment that were previously thought to be totally degraded. Perhaps the major public concern of the 1980's is protection of groundwater. The Environmental Protection Agency (EPA) estimates that 100,000 of the nation's 1.3 million wells are contaminated with pesticides (Fleming, M. H. [1987] Amer. J. Alterative Agriculture 2:124-130). This has alarmed the general public since 50% of all Americans depend on groundwater wells for their fresh water supplies. Because herbicides are so widely used in agriculture, and because they are often applied directly to the soil, the potential for movement into groundwater by leaching is perhaps greater than any other pesticide. Other inadequacies of chemical controls include lack of residual control, injury to non-target organisms, undesirable residues in harvested products, and carryover in subsequent crops. Among the chemical herbicides now being used in efforts to control Melaleuca are Arsenal (isopropylamine salt of 2-[4,5-dihydro-4-methyl-4-91-methylethyl)-5-oxo-1H-imidazol-2-yl]-3-pyridinecarboxylic acid), Bonvel 720 (diethylamine salt of 2,4-dichlorophenoxy-acetic acid+dimethylamine salt of 3,6-dichloro-0-anisic acid), Garlon 3A (triethylamine salt of 3,5,6,-tricloro-2-pyridinyloxyacetic acid), Rodeo (isopropylamineamine salt of N-(phosphonomethyl)glycine), Spike (N-[5-(1,1-dimethylethyl)-1,3,4,-thiadiazol-Z-yl]-N,N'dimethylurea), and Velpar (3-cyclohexyl-6-dimethylamino) 1-methyl-1,3,5-triazine-2,4(1H,3H)-dione). Certainly, the use of chemical herbicides must be avoided or reduced to the extent possible in the environmentally sensitive wetlands of South Florida.

Therefore, the use of bioherbicides is becoming an increasingly important alternative to chemical herbicides. This importance is exemplified by several patents which have been issued for bioherbicides and their use. Some of these patents, by way of illustration, are as follows: U.S. Pat. No. 3,849,104 (control of northern jointvetch with *Colletotrichum gloeosporioides* Penz. aeschynomene); U.S. Pat. No. 3,999,973 (control of prickly sida [teaweed] and other weeds with *Colletotrichum malvarum*); U.S. Pat. No. 4,162,912 (control of milkweed vine with *Araujia mosaic* virus); U.S. Pat. No. 4,626,271 (Cyanobacterin Herbicide); and U.S. Pat. No. 4,915,726 (Biological Control of Dodder).

*Melaleuca quinquenervia* has not been reported to have any natural enemies in Florida capable of inducing mortality. Fungi of the genus Botryosphaeria, including *B. ribis*, have been shown to grow on other species of plants (Ramos, L. J., S. P. Lara, R. T. McMillan, Jr., K. R. Narayanan [1991] Plant Dis. 75:315–318; Venkatasubbaiah, P., T. B. Sutton, W. S. Chilton [1991] Phytopath. 81:243–247; Webb, R. S. [1983] Plant Dis. 67:108–109). However, the fungus is not shown to cause sufficient damage to induce mortality in any of the specifies shown to be infected with the fungus.

Mellein and 4-hydroxymellein are isocoumarin compounds which have previously been described (Moore, J. H., N. D. Davis, and U. L. Diener [1972] "Mellein and 4-hydroxymellein production by *Aspergillus ochraceus* wilhem,' Microbiology 23(6):1067–1072; Cole, R. J., J. H. Moore, N. D. Davis J. W. Kirksey, and U. L. Diener [1971] "4-hydroxymellein: A new metabolite of *Aspergillus ochraceus* J. Agr. Food Chem., 19(5):909). Phytotoxic properties have not previously been reported for these compounds. Nor has there been any report that these compounds are produced by *Botryosphaeria ribis*.

BRIEF SUMMARY OF THE INVENTION

The subject injection pertains to a novel means for producing the phytotoxins mellein and 4-hydroxymellein as well as a highly efficient means for delivering these compounds to a target pest plant. The isocoumarin compounds mellein and 4-hydroxymellein are produced by the fungus *Botryosphaeria ribis*. In addition to the discovery that the isocoumarin compounds are produced by *B. ribis* the subject invention pertains to the means of delivering these phytotoxins to a target pest plant. Specifically, the fungus can be applied directly to a target plant, and preferably, to a wound on the plant. Growth of the fungus results in the direct administration of the phytotoxins to the target plant.

In a preferred embodiment, the subject invention concerns the discovery of a novel method for control of the exotic pest tree *Melaleuca quinquenervia*. Specifically, the subject invention pertains to a highly effective means for delivering a phytotoxin to melaleuca trees. This method has been shown to have surprising ability to provide specific control of Melaleuca trees. In this preferred embodiment of the invention, the phytotoxin of the subject invention is delivered to the Melaleuca tree by applying an effective amount of the fungus *Botryosphaeria ribis* directly to the tree. This fungus produces sufficient quantities of a phytotoxic compound to inhibit the growth or actually induce mortality of Melaleuca trees. The growth of the fungus can also mechanically disrupt nutrient transport in the vascular system of the tree.

Advantageously, the fungus may be applied to a wound in the target tree to facilitate the introduction of phytotoxin into the vascular system of the tree. These wounds may either be natural wounds or mechanically made wounds. Alternative means of introducing the fungus include, but are not limited to, transmission vectors such as parasitic or symbiotic insects.

The phytotoxic composition delivered by the methods of the subject invention comprises mellein, 4-hydroxymellein, or a combination of the two. The methods of the subject invention cause stem cankering, foliar wilt, and death of the target Melaleuca tree. These symptoms and the ultimate control of Melaleuca can be enhanced by the mechanical disruption of the tree's vascular fluid flow caused by the growth of the fungus.

DETAILED DESCRIPTION OF THE INVENTION

According to the subject invention, the isocoumarin phytotoxins mellein and 4-hydroxymellein are produced by the fungus *Botryosphaeria ribis*. This fungus can be grown directly on target plants so as to effectively deliver these phytotoxins to the plant. The phytotoxins produced according to the subject invention having the following structures:

Mellein

4-Hydroxymellein

*Botryosphaeria ribis* is unusual in its production of the trans-isomer of 4-hydroxymellein.

The subject invention provides an effective species-specific means for controlling pest trees of the species *Melaleuca quinquenervia*. Specifically, a phytotoxin, or mixture of phytotoxins is delivered to the vascular tissue of these trees. In a preferred embodiment of the subject invention, the spores or hyphae of the fungus *Botryosphaeria ribis* can be applied directly to the Melaleuca trees. This fungus produces phytotoxins which control the Melaleuca. These phytotoxins enter the vascular tissue of the Melaleuca and cause foliar wilt and mortality. This effect can be enhanced by mechanical disruption of the plant's vascular system caused by the growth of the *B. ribis*.

One of the reasons frequently mentioned for the success of *M. quinquenervia* as an invasive pest plant species was the apparent lack of mortality-inducing natural enemies. *Melaleuca quinquenervia* has not been reported previously in the literature to be colonized by microorganisms which lead to tree death.

The use of this fungus to administer the species-specific phytotoxin which incites stem cankering and, ultimately, mortality of infected *M. quinquenervia* trees is a highly advantageous means of reducing host populations. Among advantages are (1) avoidance of pesticidal contamination of waterways and wetlands, where *M. quinquenervia* grows most frequently; and (2) contribution to inoculum buildup and natural spread of the fungus from dead and moribund trees.

The phytotoxic composition of the subject invention can be delivered to the pest tree by allowing *B. ribis* to grow directly on the tree. Advantageously, the phytotoxic composition is most effectively introduced into the tree by applying the fungus to a wound on the tree. Alternative means of introducing the fungus are by transmission vectors, which can include parasitic or symbiotic insects.

A subculture of the *Botryosphaeria ribis* has been deposited in the permanent collection of the American Type Culture Collection (ATCC), 12301 Parklawn Drive, Rockville, Md. 20852 U.S.A. The culture was assigned the following accession number by the repository:

| Culture | Accession number | Deposit date |
| --- | --- | --- |
| Botryosphaeria ribis | ATCC 74057 | May 6, 1991 |

The subject culture has been deposited under conditions that assure that access to the culture will be available during the pendency of this patent application to one determined by the Commissioner of Patents and Trademarks to be entitled thereto under 37 CFR 1.14 and 35 USC 122. The deposit is available as required by foreign patent laws in countries wherein counterparts of the subject application, or its progeny, are filed. However, it should be understood that the availability of the deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep them viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restriction on the availability to the public of the subject culture deposit will be irrevocably removed upon the granting of a patent disclosing it.

*Botryosphaeria ribis* can be grown on solid or in liquid media. Solid media that can be used include water agar, potato dextrose agar, V-8 agar, and string bean agar (strained extract of macerated string beans solidified in agar). Spores are produced on solid V-8 medium exposed to fluorescent light. Specifically, solid media can be, for example, (1) water agar, (2) potato dextrose agar (Difco), (3)lima bean agar (Difco), (4) corn meal agar (Difco, (5) potato-carrot agar (Tuite 19), and (6) Desmodium agar (blend 10 g Desmodium plant parts or plant extracts in 1000 ml water and solidify with 20 g agar).

For large scale production in fermentation tanks, liquid media is used, for example:

| Formula I - Modified Richard's Solution - V-8* | |
| --- | --- |
| Sucrose | 50.00 gm |
| Potassium nitrate | 10.00 gm |
| Potassium phosphate, monobasic | 5.00 gm |
| Magnesium sulfate.7H$_2$O | 2.50 gm |
| Ferric chloride | 0.02 gm |
| V-8 juice | 15.00 ml |
| Distilled water to make | 1000.00 ml |

*Trademark, The Campbell Soup Company for mixed vegetable juices.

Formula II—Modified Richard's Solution—Distillers Solubles—Same as Formula I but substitute 15 gm Distillers solubles for V-8 juice.

Formula III—Modified Richard's Solution—Brewers yeast—Same as Formula I above but substitute 15 gm brewers yeast for V-8 juice.

Formula IV—Modified Richard'Solution—Torula Yeast—Same as Formula I above but substitute 16 gm torula yeast for V-8 juice.

Formula V—Oatmeal solution—4%+2% sugar—40 gm oatmeal, 20 sucrose, 1000 ml distilled water.

The preparation of spores is commenced in preseed liter flasks containing about 300 ml of liquid medium which have been inoculated with spores. The medium is incubated for 1–3 days with agitation at a temperature of about 26° C. to about 30° C.

The preseed is then transferred aseptically to 20 liter seed tanks with additional sterile medium as described above. The tanks are provided with sterile air and agitation. The cycle is continued at a temperature of about 26° C. to about 30° C. for 1 to 3 days.

Larger fermentors (250 liter) are aseptically inoculated with the seed tanks (entire contents), described above. Additional sterile medium, as used above, is added the pH adjusted to about 6.0. The fermentor is supplied with sterile air and agitation, and is maintained at a temperature of about 26° C. to about 30° C. for from 1 to 3 days. The fermentor is then harvested by filtering the contents to remove insoluble solids and mycelia growth. The filtered beer is then centrifuged, the supernatant is discarded, and the remaining spore concentrate is collected, placed in plastic bags, and stored in ice. The concentrate so stored maintains an 80% germination for up to 21 days.

The spore concentrate is mixed with an agriculturally acceptable diluent or carrier for application to the Melaleuca tree or a situs. By the term "situs" is meant those areas infested with the undesired tree or potential infestation sites.

The preferred carrier is water, and the spore concentrate is dispersed to make a concentration of from about $2 \times 10^4$ to $2 \times 10^7$ spores/ml. The formulation can be sprayed on the undesired tree or situs by conventional spraying equipment.

The effectiveness of the novel *B. ribis* may also be enhanced by mixing it with chemical herbicides such as 2,4-D, atrazine, linuron, paraquat, alachlor, metolachlor, glyphosate, dichlobenil, EPTC, and arsenicals.

Table 1 provides a list of other groups of herbicides which could be used in conjunction with the novel fungus of the subject invention.

TABLE 1

| Herbicide group | Example |
| --- | --- |
| Carbamate | dichlobenil |
| Thiocarbamate | EPTC |
| Substituted urea | linuron |
| Triazine | atrazine |
| Asymmetrical triazine | metribuzin |
| Substituted uracil | terbacil |
| Chloroacetamide | metolachlor |
| Acid amide | pronamide |
| Bipyridinium | paraquat |
| Sulfonyl urea | chlorsulfuron |
| Imidazoinone | imazaquin |
| Dinitroaniline | trifluralin |
| Diphenyl ethers | oxyfluorfen |
| Difenoxycarboxylic acid | fluazifop |
| Benzoic acid | amiben |
| Phenoxy | 2,4-D |
| Unclassed | glyphosate |

Though spores are the preferred form the fungi, the fungi can also be used in their vegetative form. For example, fragmented mycelia can be formulated and applied to purple nutsedge in much the same manner as described above for the spore form.

Use of the fungus Botryosphaeria ribis Grossenbacher & Duggar to introduce phytotoxins offers a safe, economical, effective, residual, and non-polluting method of reducing the population of M. quinquenervia.

Following are examples which illustrate procedures, including the best mode, for practicing the invention. These examples should not be construed as limiting. All percentages are by weight and all solvent mixture proportions are by volume unless otherwise noted.

EXAMPLE 1

Introduction of Phytotoxin Via Mechanical Wound

The introduction of a phytotoxic composition to the vascular system of Melaleuca (or other target plant) can be effectively achieved by placement of hyphae and/or spores of the fungus B. ribis into a wound in the bark of the Melaleuca. The wound may be, for example, a small mechanical wound, i.e., hole <5 mm diameter, in the stems of young Melaleuca or a large wound on an older Melaleuca. This locus of fungal inoculum rapidly spreads under the bark and colonizes xylem and phloem tissue. With inoculated seedlings, cankers develop circumferentially as well as distally toward the foliage-bearing areas of stems or branches. Canker formation interferes with water flow which can enhance the effect of the phytotoxin and eventually results in wilting, defoliation, and tree death. Within five to ten days after inoculation, seedlings are either moribund or dead.

Although sprouts occasionally develop below the point of inoculation, the fungus enters the new vascular tissue and incites cankers similar to those produced on main stems by the original inoculation. Moreover, death of the tree does not retard expansion of the fungus, whose spores can transfer to nearby trees.

When creating a mechanical wound for introduction of the fungus of the subject invention, any method can be used which penetrates the outer bark and exposes vascular tissue. It is the vascular tissue which is most susceptible to the action of the phytotoxin as well as mechanical disruption caused by the growth of the fungus. Thus a wound could be made using a knife, shears, machete, ax, or other appropriate tool, depending upon the size of the tree. Also, a composition comprising the fungus and/or phytotoxins of the subject invention may be injected into the tree using injection techniques which are well known to those skilled in this art. The fungus or phytotoxic composition may also be introduced into a naturally occurring wound on the Melaleuca tree.

EXAMPLE 2

Alternative Methods of Inoculation

In addition to introduction of a phytotoxic composition by means of applying fungi into a wound mechanically created in the pest plant species, insect vectors can be used to inoculate the plant with fungus. In this embodiment, an insect which naturally inhabits Melaleuca (or other target plant), and preferably a species of insect which prefers this plant species, can be exposed to hyphae and/or spores of the fungus which then become attached to the body of the insect. These insects which carry the fungal spores are then released into the area in need of Melaleuca control. The insects which carry the fungus introduce the fungus to the tree.

Most preferably, these insects, either as parasites or symbiotic species, bore into the tree or otherwise introduce the fungus below the protective layer of bark. The fungus, once introduced, establishes a colony on the plant species whereby the production of a phytotoxic composition by the fungus disrupts plant growth and leads to mortality of the tree.

EXAMPLE 3

Isolation and Identification of the Phytotoxins, Mellein and 4-Hydroxymellein

Mellein and 4-hydroxymellein can be isolated from culture filtrate of B. ribis using a variety of extraction procedures which are well known to those skilled in this art. For example, B. ribis cultures can be filtered through weighed 33 cm Whatman no. 2 filter papers that are dried at 70° C. for 12 hours. Mycelial mats can be washed with demineralized water, and weights determined after drying for 12 hours at 70° C. and cooling in a desiccator for one hour. Filtrates can be adjusted to their original volume with demineralized water and their pH values measured with a Corning model 12 pH meter. Filtrates can be adjusted to pH 4 and mellein and 4-hydroxymellein extracted from 25 ml of each filtrate with two 25 ml portions of chloroform in a 500 ml separatory funnel. Solid substrate can be extracted by blending with 200 ml of chloroform for 1 minute in a Waring blender. The slurry can then be filtered and the residue washed with another 100 ml of chloroform. The chloroform can be evaporated to dryness on a boiling water bath, and the residue of each flask is redissolved in 0.5 ml of chloroform. Analogous extraction procedures using ethyl acetate can also be utilized.

Identity of the extracted phytotoxin can be confirmed by TLC co-chromatography with authentic mellein and 4-hydroxymellein or by spectral analysis.

A person skilled in the art could obtain mellein and 4-hydroxymellein by growing large quantities of B. ribis and isolating the phytotoxins therefrom. The phytotoxic composition obtained in this manner could then be applied directly to melaleuca or other plants. The phytotoxins could be applied, for example, as a spray or wash administered directly to the outside of the plant or to a wound on the plant. Also, the phytotoxins could be injected into the vascular system of the plant using techniques which are well known to those skilled in the art. To apply the phytotoxin by any of these means, the phytotoxins could first be combined with appropriate agricultural carriers or other phytotoxins which are well known to those skilled in this art.

EXAMPLE 4

Herbicidal Activity of Mellein and 4-Hydroxymellein

Extracts of *B. ribis* which contain mellein and 4-hydroxymellein have been shown to be active against melaleuca and sorghum. The results are presented in Table 2.

TABLE 2

Effect of *B. ribis* cell-free culture filtrate (cf) on root growth

| Seedling | | cf (as such) | cf (5 fold conc.) | Distilled Water Control |
|---|---|---|---|---|
| Melaleuca | 24 hr | 0.0 | 0.0 | 3.0 |
| | 48 hr | 1.0 | 0.0 | 4.0 |
| | 72 hr | 1.5 | 0.0 | 6.5 |
| | 96 hr | 1.7 | 0.0 | 7.8 |
| Sorghum | 24 hr | 4.5 | 0.0 | 22.0 |
| | 48 hr | 7.5 | 0.0 | 42.0 |
| | 72 hr | 8.4 | 0.0 | 48.0 |
| | 96 hr | 8.6 | 0.0 | 63.0 |

The culture filtrate from *B. ribis* has also shown phytotoxicity on weed leaves. Specifically, the filtrate has shown phytotoxicity against sicklepod, prickly sida, and johnsongrass.

It should be understood that the examples and embodiments described herein are for illustrative purposes only and that various modifications or changes in light thereof will be suggested to persons skilled in the art and are to be included within the spirit and purview of this application and the scope of the appended claims.

I claim:

1. A process for controlling Melaleuca trees, said process comprising administering a lethal amount of a composition comprising a phytotoxin-producing fungus of the genus Botryosphaeria to said Melaleuca.

2. The process, according to claim 1, wherein said administered phytotoxin produced by said fungus comprises mellein and 4-hydroxymellein.

3. The process, according to claim 1, wherein said Melaleuca trees are *Melaleuca quinquenervia*.

4. The process, according to claim 3, wherein said fungus is administered to a wound on said *Melaleuca quinquenervia*.

5. The process, according to claim 1, wherein said fungus is formulated with an appropriate agricultural carrier.

6. The process, according to claim 3, wherein said fungus is *Botryosphaeria ribis* having the capability of producing mellein or 4-hydroxymellein characteristic of ATCC 74057.

7. The process, according to claim 1, which further comprises application of a chemical herbicide.

8. The process, according to claim 1, wherein a composition comprising an isolated fungus is administered to said Melaleuca by means selected from the group consisting of injection.

* * * * *

UNITED STATES PATENT AND TRADEMARK OFFICE
CERTIFICATE OF CORRECTION

PATENT NO. : 5,185,023

DATED : February 9, 1993

INVENTOR(S) : Roger S. Webb

It is certified that error appears in the above-identified patent and that said Letters Patent is hereby corrected as shown below:

Column 1, line 12, "mill pests" should read --kill pests--.

Column 6, line 41, "added the pH" should read --added and the pH--.

Signed and Sealed this

Thirtieth Day of November, 1993

Attest:

BRUCE LEHMAN

Attesting Officer

Commissioner of Patents and Trademarks